United States Patent [19]

Sorensen

[11] Patent Number: 4,966,744
[45] Date of Patent: Oct. 30, 1990

[54] APPARATUS AND METHOD FOR INJECTION MOULDING A THIN-WALLED CONTAINER HAVING A BASE WALL WITH A PLANAR INTERIOR SURFACE

[76] Inventor: Jens O. Sorensen, P.O. Box 2274, Rancho Santa Fe, Calif. 92067

[21] Appl. No.: 346,021
[22] PCT Filed: Oct. 7, 1987
[86] PCT No.: PCT/GB87/00710
§ 371 Date: Mar. 31, 1989
§ 102(e) Date: Mar. 31, 1989
[87] PCT Pub. No.: WO88/02686
PCT Pub. Date: Apr. 21, 1988

[30] Foreign Application Priority Data
Oct. 7, 1986 [GB] United Kingdom ............... 8624056

[51] Int. Cl.$^5$ ............................................. B29C 45/00
[52] U.S. Cl. ............................ 264/328.1; 264/336; 425/542; 425/555; 425/577
[58] Field of Search ............... 264/328.1, 2.2, 328.11, 264/328.12, 336, 328.16; 425/808, 542, 577, 555; 249/144

[56] References Cited

U.S. PATENT DOCUMENTS 3,196,483 7/1965 Eyles .
4,254,065 3/1981 Ratkowski ................... 264/328.15
4,422,998 12/1983 Sorensen ........................... 264/335
4,447,372 5/1984 Kreuttner .......................... 264/2.2

FOREIGN PATENT DOCUMENTS 1180523 1/1985 Canada .
1294162 4/1962 France .
2277149 1/1976 France .
57-205120 12/1982 Japan ................................. 264/2.2

OTHER PUBLICATIONS

F. J. Lupton, "Injection Moulds–Part 2", British Plastics, vol. 43, No. 10, Oct. 1970, pp. 142-145.
Hoechst, "Artikelgestaltung und Werkzeugkonstruktion bei der Spritzgussverarbeitung von Niederdruck-Polyäthylen und Polypropylen", Der Plastverarbeiter, vol. 12, No. 10, Oct. 1961, pp. 453-454.

Primary Examiner—Jill L. Heitbrink
Attorney, Agent, or Firm—Edward W. Callan

[57] ABSTRACT

Apparatus for moulding a thin-walled article, such as a Petri disk, in which the moulding is effected by injecting from the side of a planar portion of the article. The moulding apparatus has a core piece (10) co-operable with a cavity (12) which together define a space (14) in which the article is to be moulded. At least one of the core (10) or the cavity (12) has a moulding surface (16, 18), corresponding to the planar portion of the finished article, which is non-planar. Preferably, the moulding surface (18) of the cavity (12) has a concave curvature, while the opposing surface (16) of the core (10) inserted therein has a convex curvature. The radius of curvature preferably being larger at the core than at the cavity. The particular configuration allows more material to be supplied to the central area corresponding to the planar portion of the finished article. This material cools more slowly than other portions of the article causing contraction so that the planar portion of the finished article is substantially flat.

14 Claims, 1 Drawing Sheet

APPARATUS AND METHOD FOR INJECTION MOULDING A THIN-WALLED CONTAINER HAVING A BASE WALL WITH A PLANAR INTERIOR SURFACE

This invention relates to an improved apparatus for moulding a thin-walled article such as a Petri dish or other product which is injected from the side during moulding; and to a method of moulding such an article.

Petri dishes are well known and widely used, especially in biological laboratories for producing cultures of mirco-organisms in a culture medium, such as agar. It is important that the base of the inside of the dish is substantially flat so as to allow a thin, uniform layer of the culture medium while using as little of the medium as possible. This ensures uniform light transmission through the medium over the whole area of the dish, which is important for accurate assessment of the development of the culture. Furthermore, when the base is substantially flat, considerable savings may be made on the usage of the medium in order to cover the whole base area with fluid.

A Petri dish must be injected from the side during moulding because the injection gate to the cavity leaves an impression which would confuse accurate assessment of the culture in the dish. Because the Petri dish must be injected from the side a major problem with existing manufacturing methods is that the base of the dish tends to assume a significant curvature after removal from the mould. The mould traditionally has planar moulding surfaces corresponding to the surfaces of the base of the Petri dish which is to be planar and, in order to prevent unacceptable curvature, the problem has been dealt with by thickening the walls of the dish and increasing the cooling time before it is ejected from the mould. However these solutions are unsatisfactory because they involve the use of more material than required for the mechanical strength of the finished article; and they lengthen the mould residence time, thereby making the process expensive while lowering the production rate of the mould.

This invention seeks to overcome or mitigate these drawbacks with an apparatus which allows satisfactory Petri dishes to be produced at a considerably higher rate, and lower cost, than present apparatus.

According to this invention, an apparatus for moulding by injecting from the side of a planar portion of a thin-walled article, such as a Petri dish, comprises a core piece co-operable with a cavity and defining a space between in which an article is to be moulded, at least one of the core or the cavity having a moulding surface, corresponding to the planar portion of the finished article, which is non-planar.

In a preferred embodiment of the invention, the moulding surface of the cavity has a concave curvature, while the opposing surface of the core inserted therein has a convex curvature. In this embodiment, the radius of curvature of the moulding surface of the cavity is less than that of the opposing core surface.

In alternative embodiments, these radii may be the same, or the moulding surface of the core may be flat or may have a concave curvature. In the cases where the core is concave we have observed that the cavity may be flat or even slightly convex.

The invention also includes a method of moulding by injecting from the side of a planar portion a thin-walled article, such as a Petri dish which has a flat base, comprising the steps of forming the article in a mould whose shape is such that the planar portion initially has a central region which is thicker than the regions near the side or rim.

In the moulding lids in soft plastics material for containers where visual distortion is not a problem it is known to centre-inject plastics material and mould the surface with a curve. However, this is done for a completely different purpose from the present invention. With the lid, where injection is from the centre, the centre is hotter than the rim when the lid is ejected from the mould. Thus the centre area tends to shrink more than the rim so that, if moulded flat, a lid with a saddle shape would be produced because, with shrinkage, there is effectively too little material area left in the centre. In order to present this adverse shaping it is known to add more plastics material area at the middle by curving to compensate for the shrinkage which does occur.

In the present invention a different problem is being addressed. Because with the dish, which is made of hard plastics as opposed to the above-mentioned lid which is made of soft plastic, it is important to inject from the side, with side injection there is a tendency for the hard plastic rim of the dish to pull the centre of the base up between the sides of the rim. Thus, there is the opposite problem that there is effectively too much material area in the centre of the base. In order to compensate or counter for this factor the hard plastic base of the Petri dish is moulded with a curve which is opposite to the way in which the base tends to be drawn between the sides of the rim. Further the present invention proposes to increase the wall thickness at the centre of the base to actually make the centre undergo shrinkage.

The invention will now be described by way of example with reference to the accompanying drawings in which.

Figure 1:
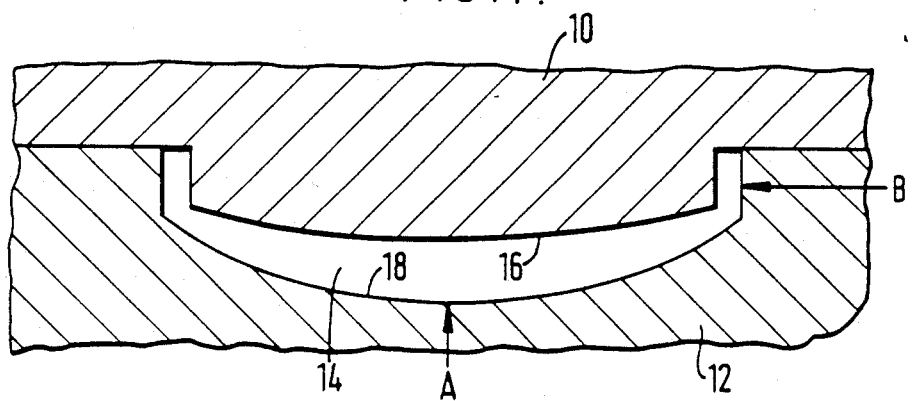
FIG. 1 is a schematic cross-sectional view of a moulding apparatus in accordance with the invention, showing a preferred embodiment.

Referring to FIG. 1 of the drawings, a preferred embodiment of moulding apparatus for the invention comprises a core piece 10 which fits within a cavity piece 12, thereby substantially defining the shape of the dish within the space 14 between. The core piece 10 has a convex surface 16 which corresponds to the inside surface of the base of the dish, while the cavity piece 12 has a concave surface 18 which corresponds to the outer surface of the base. The convex surface 16 has a radius of curvature greater than that of the concave surface 18 thereby producing a base wall which is thicker in the middle than at the edges. Typical values, for the case of a 9 centimeter dish, of the radii of curvature are 2.5 meters and 1.5 meters for the core and cavity respectively, while the base wall is typically 0.6 mm thick in the middle and 0.4 mm thick at the edges. It is emphasised that the drawings are not to scale and that they exaggerate these differences for clarity.

Arrow A shows the central and conventional position of the gate suited for most products. Arrow B shows the side position of the gate which is necessary when injection moulding a Petri dish.

In an alternative arrangement (not shown), the radius of curvature of the convex surface 16 equals that of the concave surface 18.

Figure 2:
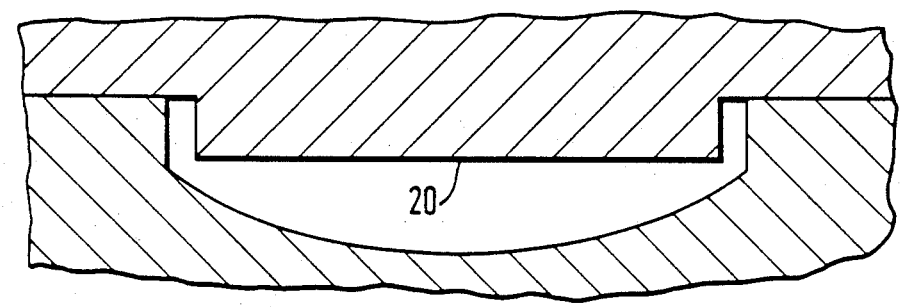
FIG. 2 is a schematic cross-section view of a second embodiment of the invention.
Figure 3:
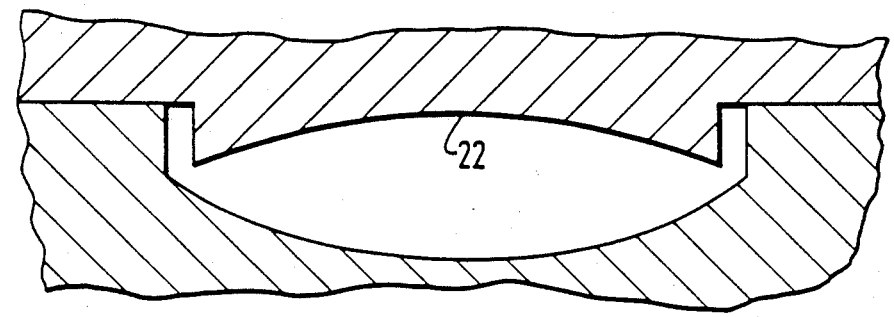
FIG. 3 is a schematic cross-sectional view of a third embodiment of the invention.

Another embodiment of the invention, shown in FIG. 2, shares the concave cavity surface 16 with the preferred embodiment described above, but employs a core with a planar corresponding surface 20. A further embodiment, shown in FIG. 3, employs a similarly-shaped cavity but has a core with a concave, base surface 22.

If a Petri dish could be moulded from the centre of the base of the dish then when injected, it would be warmer near the centre and therefore contracting in this warm area thereby keeping the base flat.

In the method of the invention plastics material is fed to the space 14 through a side injected runner system diagrammatically indicated by Arrow B. By producing a base wall which is thicker in the middle than at the edges, the central portion of the wall cools less rapidly than the edges having a smaller surface area-to-volume ratio. The contraction associated with this slower cooling draws the base into a substantially flat configuration, shortly after ejection from the mould.

9 cm diameter transparent polystyrene Petri dishes, manufactured using prior art apparatus, must typically weigh 15 to 18 grams and have a cycle time of 5 to 6 seconds, in order to achieve an acceptable flat inner base wall. By employing a prefered embodiment of the invention, this flatness may be maintained within tolerances of 0.3 mm convex and 0.4 mm concave, while reducing the weight and the cycle time to within 9 grams and 2.5 seconds respectively. This reduction of material usage, and production time, per unit will produce cost savings over large production volumes.

I claim:

1. An method of moulding by side injection a thin-walled container having a base wall with planar surface and side walls, comprising the steps of forming the container with a core piece co-operable with a cavity piece and defining a space therebetween in which said container is to be moulded: and filling the space with heated plastic material injected through a gate located adjacent the space defining the side walls, wherein a surface of the cavity piece for forming an exterior base wall of the container is concave so that when the container has cooled the base wall is substantially planar.

2. An method according to claim 1, wherein the base-wall-defining surface of the core piece is substantially planar.

3. An method according to claim 1, wherein the base-wall-defining surface of the core piece has a convex curvature.

4. A method of moulding by side injection a thin-walled container having a base wall with a planar interior surface and side walls, comprising
   providing a core piece having a first base-wall-defining surface;
   providing a cavity piece having a second base-wall-defining surface;
   wherin said core piece and said cavity piece cooperating to define a space forming said base wall and said side walls;
   providing a gate located adjacent the side walls forming space;
   wherein the base wall forming space having a thickness in a middle portion larger than the thickness of another portion of the base wall forming space adjacent the side walls forming space; and
   injecting said space with heated plastic material so that upon said space being filled with said heated plastic material injected through the gate, the base wall of the container cools less rapidly in the middle than at the sides such that the base wall is substantially planar after said container has cooled.

5. A method according to claim 4, wherein the base-wall-defining surface of the core piece has a convex curvature and the base-wall-defining surface of the cavity piece has a concave curvature.

6. A method according to claim 4, wherein the base-wall-defining surface of the core piece is substantially planar and the base-wall-defining surface of the cavity piece has a concave curvature.

7. A method according to claim 4, wherein the base-wall-defining surface of the core piece has a concave curvature and the base-wall-defining surface of the cavity piece has a concave curvature.

8. An apparatus for moulding by side injection a thin-walled container having a base wall with a planar surface and side walls, comprising
   a core piece co-operable with a cavity piece and defining a space therebetween in which said container is to be moulded; and
   means for filling the space with heated plastic material injected through a gate located adjacent the space defining the side walls,
   wherein a surface of the cavity piece for forming an defining the exterior base wall of the container is concave so that when the container has cooled the base wall is substantially planar.

9. An apparatus according to claim 8, wherein a base-wall-defining surface of the core piece is substantially planar.

10. An apparatus according to claim 8, wherein a base-wall-defining surface of the core piece has a convex curvature.

11. An apparatus for moulding by side injection a thin-walled container having a base wall with a planar interior surface and side walls, comprising
    a core piece having a first base-wall-defining surface;
    a cavity piece having a second base-wall-defining surface;
    said core piece and said cavity piece cooperating to define a space forming said base wall and said side walls;
    a gate located adjacent the side walls forming space;
    the base wall forming space having a thickness in a middle portion larger than the thickness of another portion of the base wall forming space adjacent the side walls forming space so that upon said space being filled with heated plastic material injected through the gate adjacent the side walls, the base wall of the container cools less rapidly in the middle than at the sides such that the base wall is substantially planar after said container has cooled.

12. An apparatus according to claim 11, wherein the base-wall-defining surface of the core piece has a convex curvature and the base-wall defining surface of the cavity piece has a concave curvature.

13. An apparatus according to claim 11, wherein the base-wall-defining surface of the core piece is substantially planar and the base-wall-defining surface of the cavity piece has a concave curvature.

14. An apparatus according to claim 11, wherein the base-wall-defining surface of the core piece has a concave curvature and the base-wall-defining surface of the cavity piece has a concave curvature.

* * * * *

UNITED STATES PATENT AND TRADEMARK OFFICE
CERTIFICATE OF CORRECTION

PATENT NO.  : 4,966,744

DATED       : October 30, 1990

INVENTOR(S) : JENS OLE SORENSEN

It is certified that error appears in the above-identified patent and that said Letters Patent is hereby corrected as shown below:

Column 1, line 60, --of-- should be inserted after "that".

Column 4, line 29 (line 11 of Claim 8), "defining the" should be deleted.

Signed and Sealed this

Nineteenth Day of May, 1992

Attest:

DOUGLAS B. COMER

*Attesting Officer*    Acting Commissioner of Patents and Trademarks